(12) United States Patent
McGhee et al.

(10) Patent No.: US 6,613,980 B1
(45) Date of Patent: Sep. 2, 2003

(54) ENVIRONMENTAL PROTECTION FOR AN OPTICAL ASSEMBLY AND METHOD THEREFOR

(75) Inventors: Andrew McGhee, Stowmarket (GB); Daniel John Keeble, Felixstowe (GB); Fabio Pozzi, Turin (IT); Brian Lemoff, Union City, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/095,022

(22) Filed: Mar. 11, 2002

(51) Int. Cl.[7] .............................. H01L 23/28; H05K 5/06
(52) U.S. Cl. .................... 174/52.2; 174/52.4; 257/433; 257/788
(58) Field of Search ................................ 257/433, 680, 257/787, 788–434; 174/52.4, 52.2

(56) References Cited

U.S. PATENT DOCUMENTS 6,246,123 B1 * 6/2001 Landers, Jr. et al. ........ 257/787
2001/0035573 A1 * 11/2001 Weigert ...................... 257/680

* cited by examiner

Primary Examiner—Hung V. Ngo

(57) ABSTRACT

A package for an optical assembly of a type that uses bulk optics in an optical path will require environmental protection from contaminants. It is common to construct a substantially hermetically sealed package to provide environmental protection for the optical assembly but such hermetically sealed packages are expensive to construct and are not completely reliable. Consequently, a package is provided for an optical assembly with the bulk optics encapsulated by a silicone encapsulant and encased within an epoxy layer and supported by a substrate base. The package for the optical assembly thus provides the bulk optics with the required environmental protection from contaminants.

8 Claims, 2 Drawing Sheets

ENVIRONMENTAL PROTECTION FOR AN OPTICAL ASSEMBLY AND METHOD THEREFOR

FIELD OF THE INVENTION

The present invention relates to an environrimental protection apparatus for an optical assembly of a type that uses bulk optics in an optical path. The present invention also relates to a method of manufacturing an environmental protection apparatus for an optical assembly.

DISCUSSION OF THE BACKGROUND ART

It is well known that both the operational efficiency and the working lifetime of an optical assembly are dependent upon the environmental conditions within which the optical assembly operates. Contaminants such as non-inert gases or moisture that come into contact with parts of the optical assembly can cause degradation and/or irreparable damage of the parts of the optical assembly.

FIG. 1 is a schematic diagram of a known package used in the art to provide environmental protection for an optical assembly. The optical assembly is substantially hermetically sealed within a housing 10 by a lid 8 to create a substantially hermetically sealed package containing a controlled gas environment 11 therein. The optical assembly comprises a bulk optical component 12 formed from a polymer such as polycarbonate and through which electromagnetic radiation 13, typically light, can propagate. The bulk optical component 12 comprises a reflecting surface 14 (by virtue of total internal reflection) which is substantially planar in shape and a lens portion 16. The optical assembly also comprises an optoelectronic device 18 disposed adjacent and beneath the lens portion 16 of the bulk optical component 12.

In operation, electromagnetic radiation 13 is divergent on leaving an optical fibre (not shown) and when entering the bulk optical component 12. The electromagnetic radiation 13 is incident upon the reflecting surface 14 and, via total internal reflection of the electromagnetic radiation 13, the electromagnetic radiation 13 is reflected to the lens portion 16. The lens portion 16 focuses the electromagnetic radiation 13 onto the optoelectronic device 18.

Although a near contaminant free, controlled, gas environment 11 can be achieved by the near-hermetic seal between the lid 8 and the housing 10, some ingress of contaminants and moisture into the sealed package will occur as the seal is not perfect. Similarly, if the near-hermetic seal between the lid 8 and the housing 10 fails, ingress of non-inert gases and moisture into the housing will occur, thereby contaminating the controlled gas environment 11 of the package. Consequently, over time, the performance of the optical assembly degrades and the bulk optical component 12 and the optoelectronic device 18 become damaged due to the ingress of contaminants. Furthermore, production of the near-hermetically sealed package having the controlled gas environment 11 is costly and time consuming. Also, the location of the optoelectronic device 18 beneath the lens portion 16 of the bulk optical component 12 makes visual alignment of the optoelectronic device 18 with the bulk optical component 12, so that the electromagnetic radiation 13 is incident upon the optoelectronic device 18, very difficult due to the bulk optical component 12 obscuring the view of the optoelectronic device 18. The difficulty in visual alignment of the bulk optical component 12 with the optoelectronic device 18 increases the time and costs associated with the production of the packaged optical assembly.

SUMMARY OF THE INVENTION

According to the present invention, there is provided a package for an optical assembly comprising an optoelectronic device, characterised in that the bulk optical component and the optoelectronic device are enveloped by an encapsulant material having a substantially same refractive index as the bulk optical component, the bulk optical component having a reflective surface to, when in use, reflectively direct electromagnetic radiation incident thereupon to the optoelectronic device.

Preferably, the encapsulant material is silicone.

Preferably, the reflective surface is curved so as to focus the electromagnetic radiation. More preferably, the reflective surface is metallised.

According to the present invention, there is also provided a method of forming a package for an optical assembly, the method comprising the steps of: disposing an optoelectronic device on a substrate; aligning the bulk optical component with respect to the optoelectronic device, the optoelectronic device not being obscured by the bulk optical component during the alignment of the bulk optical component with the optoelectronic device; enveloping the bulk optical component and the optoelectronic device with an encapsulant material; and depositing a protective layer over the encapsulant material.

It is thus possible to provide a packaged optical assembly with effective environmental protection of the parts of the optical assembly by the envelopment of the optical assembly with silicone. Furthermore, visual alignment of the optoelectronic device with the bulk optical component, so that the electromagnetic radiation is incident upon the optoelectronic device, is simplified due to the position of the optoelectronic device relative to the bulk optical component being such that the view of the optoelectronic device is not obscured during alignment. The visual alignment of the optoelectronic device with the bulk optical component can be performed in a gaseous environment prior to envelopment of the optical assembly with silicone because electromagnetic radiation exiting the bulk optical component does so substantially normal to the surface of the bulk optical component.

At least one embodiment of the invention will now be described, by way of example only, with reference to the accompanying drawing, in which:

DETAILED DESCRIPTION OF THE INVENTION

Figure 1:
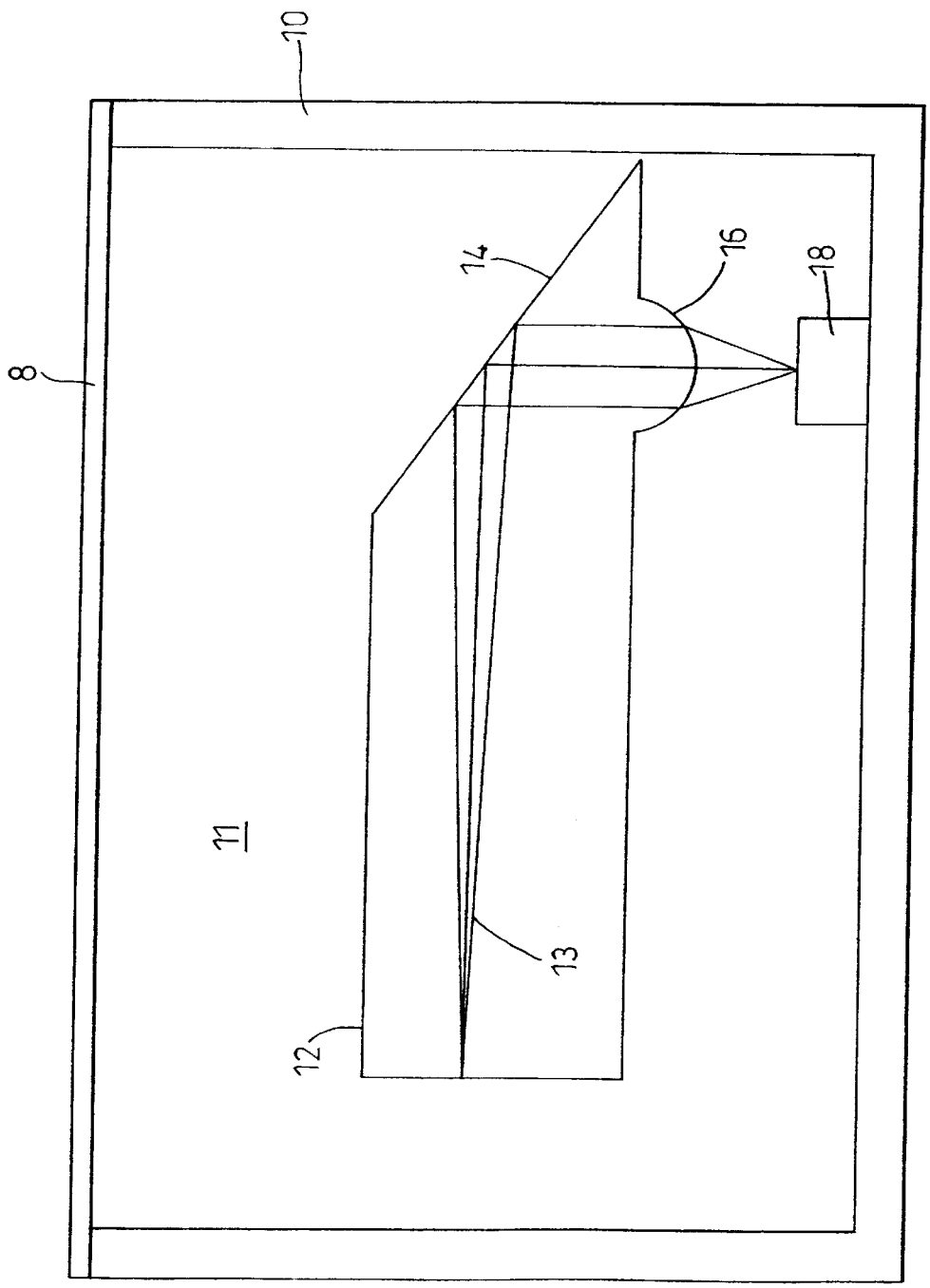
FIG. 1 is a schematic diagram of a known package used in the art to provide environmental protection for an optical assembly.
Figure 2:
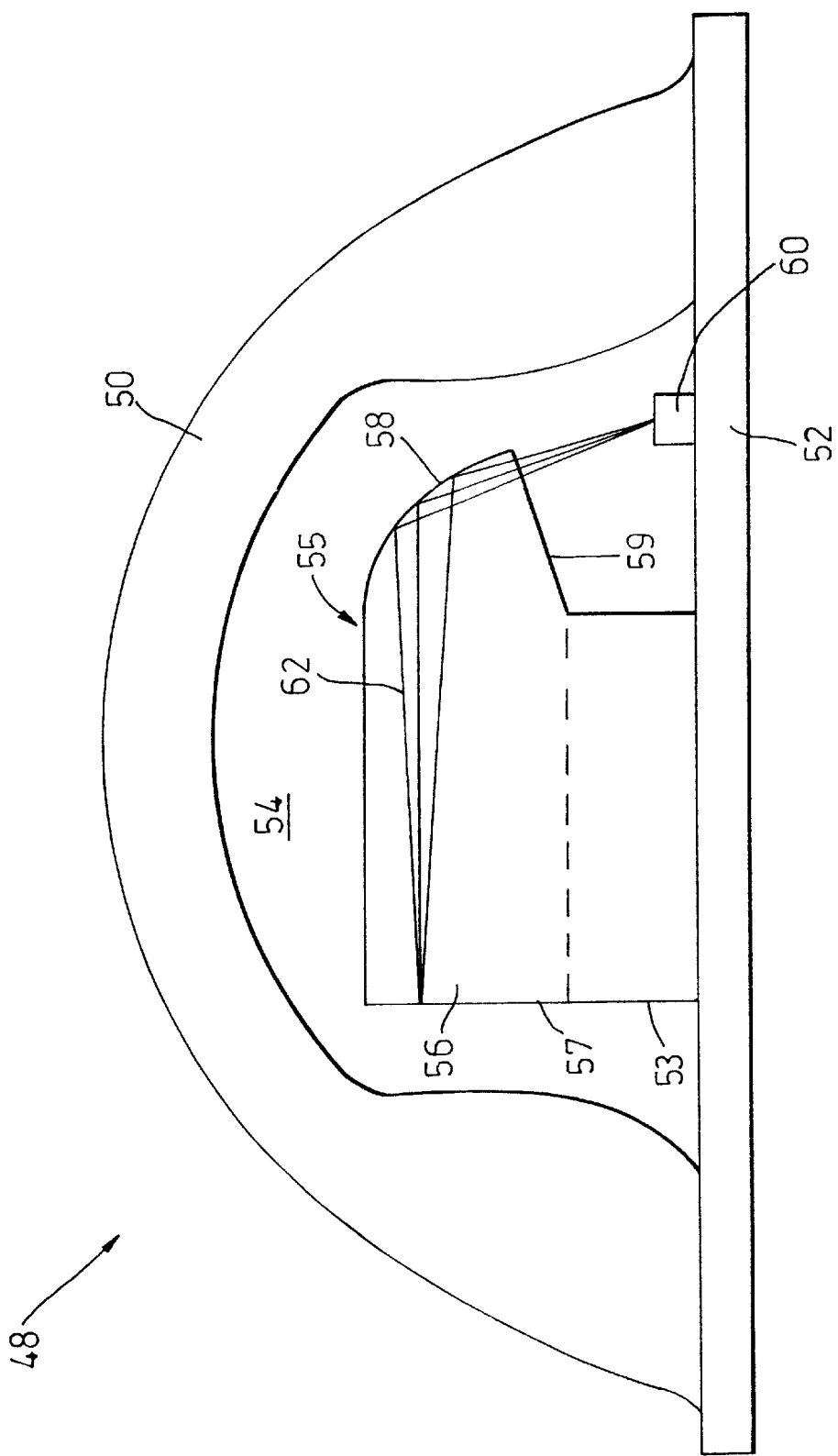
FIG. 2 is a schematic diagram of a package for an optical assembly constituting an embodiment of the present invention.

Referring to FIG. 2, a package 48 for an optical assembly comprises a substrate 52 upon which an optoelectronic device 60 is bonded. The optoelectronic device 60 lies below, and is offset slightly to one side of, a bulk optical component 56. The bulk optical component 56 can be constructed from, but is not limited to, a solid polymer such as polycarbonate through which electromagnetic radiation 62, such as light, propagates.

In this example, the bulk optical component 56 comprises an elongate body 55 having a flat first end 57 substantially perpendicular to a longitudinal axis of the body 55. The bulk optical component 56 also comprises a spacer portion 53 to support the body 55 above the substrate 52. A, second, distal end with respect to the first end has a curved surface 58, the exterior of which is metallised, and a flat surface 59 serving as a window through which electromagnetic radiation 62, reflected by the metallised curved surface 58, passes.

The reflective surface 58 is metallised using any suitable technique known in the art. A silicone encapsulant 54 of a substantially the same refractive index as the bulk optical component 56 envelops the bulk optical component 56 and the exposed surfaces of the optoelectronic device 60. An epoxy layer 50 overcoats the silicone encapsulant; the epoxy layer 50 can be formed from, but is not limited to, Hysol.

Manufacture of the optical assembly is as follows. The optoelectronic device 60 is bonded to the substrate 52 and the bulk optical component 56 aligned with respect to the optoelectronic device 60 using any suitable known alignment process, for example in a gaseous environment. The bulk optical component 56 is fixed to the substrate 52, for example, by bonding the spacer portion 53 to the substrate 52 using a light curable epoxy resin. Alignment in the gaseous environment is possible due to an optical path for the electromagnetic radiation being substantially normal to the flat surface 59 of the window of the bulk optical component 56. Since the bulk optical component 56 is arranged to focus light to a position not directly therebeneath, and hence not obscured by the bulk optical component 56, the optoelectronic device 60 is visible, i.e. not obscured, during alignment of the bulk optical component 56 with respect to the optoelectronic device 60. Once the bulk optical component 56 is aligned with the optoelectronic device 60, a glob of the silicone encapsulant 54 is deposited on the substrate 52 and over the bulk optical component 56 and optoelectronic device 60. The epoxy layer 50 is then deposited over the silicone encapsulant 54 and left to harden. Consequently, the epoxy layer 50 bonds to the substrate 52.

In operation, electromagnetic radiation 62, such as light, is divergent on leaving an optical fibre (not shown) and when entering the bulk optical component 56. The optical fibre is coupled to the bulk optical component 56 by adhering the optical fibre in a V-groove (not shown) formed within the bulk optical component using an optically clear light curable resin. The electromagnetic radiation 62 is incident upon the metallised reflective surface 58, and reflected and focussed by the metallised reflective surface 58, onto the optoelectronic device 60. The shape of the metallised surface 58 is designed to ensure that the central ray, in terms of geometric optics, of the electromagnetic radiation 62 exiting the bulk optical component 56 through the flat surface 59 (serving as the window) does so perpendicular to the flat surface 59 of the bulk optical component 56.

The silicone encapsulant 54 has optical properties that closely match the optical properties of the bulk optical component 56. Consequently, refraction cannot be used to focus the electromagnetic radiation 62 onto the optoelectronic device 60 because, despite experiencing a change in medium as the electromagnetic radiation 62 propagates from the bulk optical component 56 to the silicone encapsulant 54, the electromagnetic radiation 62 does not encounter a change in refractive index which is required for focussing in this way. Hence, the exterior of the curved surface 58 is metallised.

We claim:

1. A package for an optical assembly comprising:

an optoelectronic device; and a bulk optical component, and wherein the bulk optical component and the optoelectronic device are enveloped by an encapsulant material having a substantially same refractive index as the bulk optical component, wherein the bulk optical component has a metallised reflective surface to, when in use, reflectively direct electromagnetic radiation incident thereupon to the optoelectronic device.

2. A package as claimed in claim 1, wherein the encapsulant material is silicone.

3. A package as claimed in claim 1, wherein the metallised reflective surface is curved so as to focus the electromagnetic radiation.

4. A package as claimed in claim 3, wherein the metallised reflective surface is concave.

5. A method of forming a package for an optical assembly, the method comprising:

disposing an optoelectronic device on a substrate;

aligning a bulk optical component with respect to said optoelectronic device, said optoelectronic device not being obscured by said bulk optical component during the alignment of said bulk optical component with said optoelectronic device, wherein the bulk optical component has a metallised reflective surface to, when in use, reflectively direct electromagnetic radiation incident thereupon to the optoelectronic device;

enveloping said bulk optical component and said optoelectronic device with an encapsulant material; and depositing a protective layer over said encapsulant material.

6. A method as claimed in claim 5, wherein said encapsulant material is silicone.

7. A method as claimed in claim 5, wherein said metallised reflective surface is curved so as to focus the electromagnetic radiation.

8. A method as claimed in claim 7, wherein said metallised reflective surface is concave.

* * * * *